United States Patent [19]

Task et al.

[11] 4,377,341

[45] Mar. 22, 1983

[54] SYSTEM FOR MEASURING ANGULAR DEVIATION IN A TRANSPARENCY

[75] Inventors: Harry L. Task, Dayton; Louis V. Genco, Enon; Kenneth L. Smith; Albert G. Dabbs, both of Dayton, all of Ohio

[73] Assignee: The United States of America as represented by the Secretary of the Air Force, Washington, D.C.

[21] Appl. No.: 242,816

[22] Filed: Mar. 11, 1981

[51] Int. Cl.³ .......................................... G01N 21/88
[52] U.S. Cl. .................................... 356/239; 356/371
[58] Field of Search ............... 356/239, 371, 430, 431; 250/562, 572

[56] References Cited

U.S. PATENT DOCUMENTS 3,578,869  5/1971  Irland et al. ...................... 356/239
3,688,235  8/1972  Migeotte ........................... 356/239
4,249,823  2/1981  Task ................................... 356/128
4,255,055  3/1981  Schave ........................... 356/239 X
4,310,242  1/1982  Genco et al. ................... 356/239 X Primary Examiner—John K. Corbin
Assistant Examiner—Matthew W. Koren
Attorney, Agent, or Firm—Donald J. Singer; John R. Flanagan

[57] ABSTRACT

An improved system for measuring absolute angular deviation through transparencies, such as aircraft windscreens, uses an incoherent light source and a target configuration in the form of an opaque slide with a transparent "L"-shaped pattern. The positions of images of the legs of the "L" passed through the transparency are detected by CCD arrays for measurement of the azimuth and elevation components of angular deviation for each tested point on the transparency, uncontaminated by lateral displacement errors.

6 Claims, 6 Drawing Figures

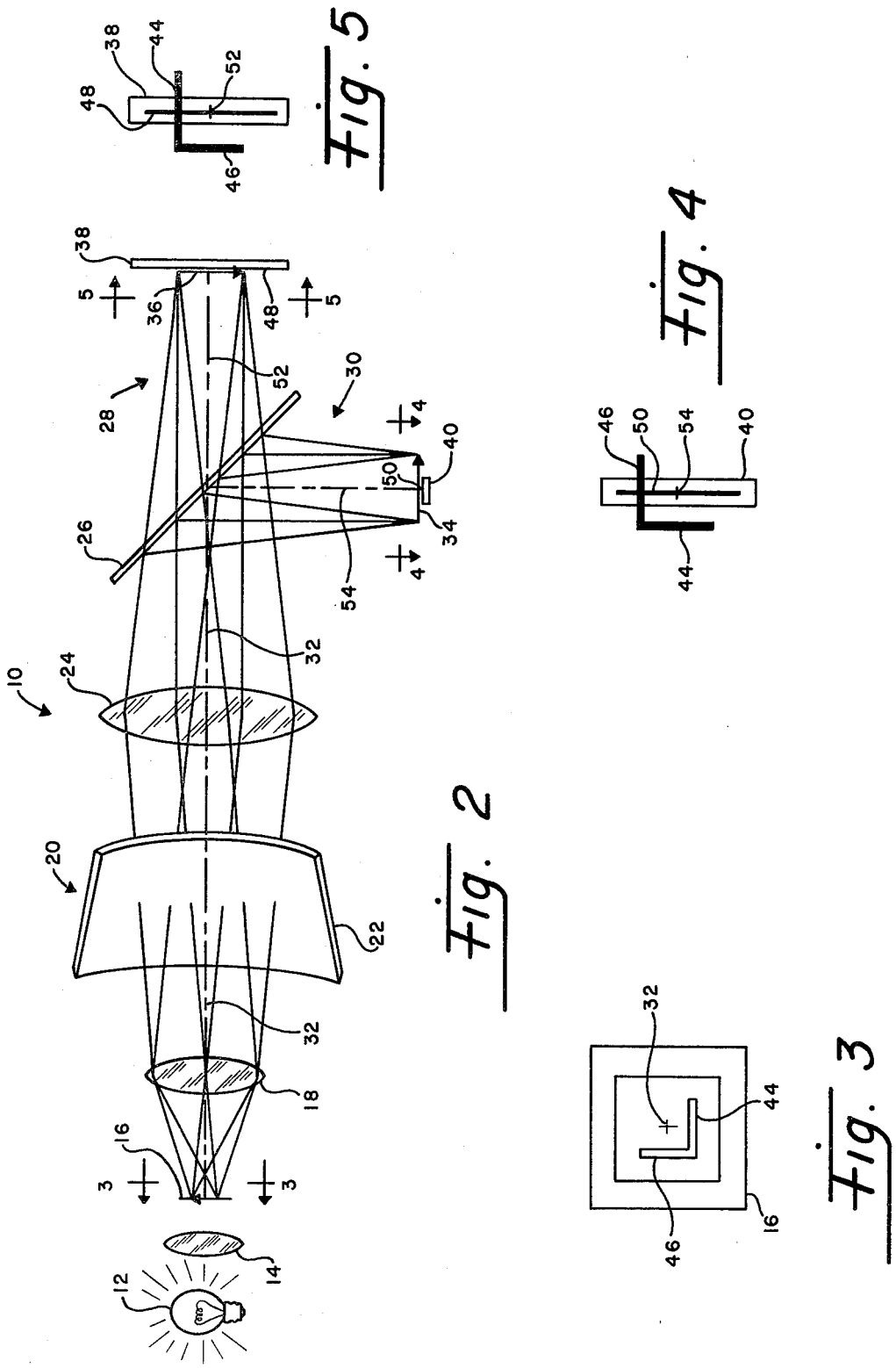

SYSTEM FOR MEASURING ANGULAR DEVIATION IN A TRANSPARENCY

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to the measurement of distortion in a transparency and, more particularly, is concerned with a system for measuring absolute angular deviation in transparencies, such as an aircraft windscreen or a helmet visor.

2. Description of the Prior Art

As a general rule, optically transparent, asymmetrically contoured bodies have been difficult to quantitatively evaluate and compare on the basis of their optical characteristics. A prime example of a structural element formed of a transparent medium in which optical quality is critical, yet difficult to quantitatively evaluate, is the canopy or windscreen of aircraft having complex curvilinear contours.

Distortion is one of the optical quality parameters that has been identified for characterizing transparencies, such as aircraft windscreens. Distortion is the non-linear mapping of object points to image space due to the optical effects of the transparency. Such effects may be due to either optical index variations in the transparency or to the opposite faces of the transparency being non-parallel. In the case of a perfect non-distorting transparency, a square grid object would be reproduced as an identical square grid in the image plane. Where there is index variation or non-parallelism between opposite faces of the transparency, the square grid will be reproduced in a distorted form in the image plane.

The visual effects of distortion, when present, are thus apparent even to untrained observers. However, quantifying the distortion to ascertain its severity is a difficult problem. Since distortion is the non-linear mapping of objects viewed through the transparency, the actual physical positions of the objects do not linearly correspond to their apparent locations as seen through the transparency. This effect can be especially detrimental to accurate aligning through an aircraft transparency of any device within the aircraft, for instance a heads-up display gun sight reticle with a target outside the aircraft.

In a more technical vein, distortion has been defined as the rate of change of angular deviation across the transparency. Angular deviation is defined as the angular deflection or change of direction of a light ray as it passes through the transparency. Theoretically, the distortion in any transparency may be determined by mapping at a plurality of locations on the transparency the angular deviation of light rays as they are transmitted from the object through the transparency to the observer.

Angular deflection of the light ray should not be confused with displacement of the light ray which is simply a lateral shift. Whenever a ray of light passes through a transparency at an angle other than normal (or perpendicular to the faces of the transparency), lateral displacement of the ray by a relatively small and constant amount results. However, whenever a ray of light passes through the transparency at the same angle, but where the opposite faces of the transparency are non-parallel, both lateral displacement and angular deflection result (FIG. 1). While lateral displacement is usually operationally insignificant beyond a few meters, the distance between the real location of the object and its apparent (deflected) position increases as the range of the object from the observer increases. Consequently, a method of quantifying the distortion in a transparency to ascertain its severity, especially in aircraft transparencies, is a necessity.

Several methods of measuring angular deviation have been employed in the past. One method uses a telescope or theodolite to view a reference target without the transparency. Then the transparency is interposed, and the target is viewed through several predetermined locations of the transparency. The difference in angular position of the target as seen with and without the transparency is a measure of the total deviation induced by the transparency. This total deviation measure unfortunately includes the effects of both lateral displacement and angular deviation. Also, measurements through areas of the transparency which cause image blurring or doubling are extremely difficult when using a telescope to look through such transparency areas.

An alternative to the telescope method involves projecting a laser beam through the transparency onto a screen. The position of the laser spot is compared to its position prior to insertion of the transparency, and the angular deviation may be calculated using trigonometry and the distance from the windscreen to the measurement screen. Although image blurring or doubling will influence the size and shape of the laser spot, it is easier to estimate the center of the distorted spot on the screen than to see the degraded image in the telescope-based system.

Both telescope-based and laser-based systems commonly reduce the contaminating effect of lateral displacement on angular deviation measures by viewing (or projecting) the image over a long distance—approaching 100 feet. For these systems, therefore, the total deviation measured is primarily due to the angular deviation and not the displacement. However, an obvious disadvantage of systems incorporating long "throw" distances in their test setups is the requirement for a large empty space, clear of obstructions, which may conflict with other functions of the facility in which the test apparatus is housed.

Furthermore, while more accurate angular deviation measurements may be obtained with a laser-based system such as the one disclosed in U.S. Pat. No. 4,249,823 to Harry L. Task and assigned to the assignee of the subject invention, a system of this particular type suffers from problems caused by the coherent nature of the laser beam in being projected upon a transmission diffraction grating. Specifically, the fan line of luminous energy generated by the grating has a speckled nature. This causes the reading produced by a linear detector array which detects the point at which the fan line crosses the array to incorporate random error within it.

SUMMARY OF THE INVENTION

The present invention obviates the foregoing disadvantages of the prior art systems by providing an improved angular deviation measurement system which uses incoherent light and a unique target configuration and achieves excellent accuracy and repeatability without requiring a large test space or a laser beam. The system is more economical and less tedious than one using a laser and permits accurate absolute angular deviation measurements to be made in a relatively short distance on aircraft windscreens oriented in the installed position. The unique target configuration is an opaque slide with a transparent pattern in the shape of an "L". Images of the legs of the "L" are used to detect and measure the azimuth (horizontal) and elevation (vertical) components of angular deviation for each tested point on the windscreen.

Accordingly, the present invention provides an improved system for measuring angular deviation in a transparent medium, which comprises the combination of: (a) an opaque object, such as a target slide, having a transparent pattern formed therein by a pair of transversely-aligned linear segments; (b) means for illuminating the transparent pattern with incoherent light; (c) means for projecting an image of the transversely-aligned segments through a test region of space; (d) means for receiving the projected image after it has passed through the test region and for transmitting it into first and second channels having first and second optical axes, respectively; and (e) first and second linear detector arrays located respectively along the first and second optical axes for facilitating detection and measurement of aximuth and elevation components of angular deviation for each tested point on a transparency, such as an aircraft windscreen, positioned in the test region. The first detector array is located along the first optical axis in the focal plane of the image of the transparent pattern across its one linear segment, while the second detector array is located along the second optical axis in the focal plane of the image of the transparent pattern across its other linear segment. The first and second detector arrays detect lateral shifts in the positions of the respective images of the transparent pattern linear segments which correspond to azimuth and elevation components of angular deviation for a particular point on the transparency, the lateral shifts occurring, if at all, when the transparency is inserted into the test region.

BRIEF DESCRIPTION OF THE DRAWINGS

FIG. 2 is a plan view in schematical form of the improved angular deviation measurement system of the present invention.

FIG. 3 is an enlarged view as seen along line 3—3 of FIG. 2 of the target slide used in the improved measurement system.

FIG. 4 is a schematical representation as seen along line 4—4 of FIG. 2 of the intersection of the image of the "L"-shaped transparent pattern of the opaque target slide with the vertical or elevation detector array.

FIG. 5 is a schematical representation as seen along line 5—5 of FIG. 2 of the intersection of the image of the "L"-shaped transparent pattern of the opaque target slide with the horizontal or azimuth detector array.

DETAILED DESCRIPTION OF THE INVENTION

Figure 1:
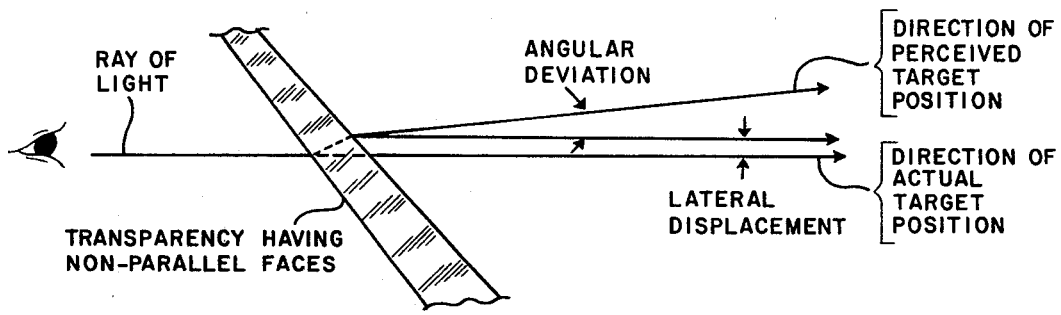
FIG. 1 is a schematical representation of the lateral displacement and angular deflection of a ray of light passing through a transparent medium having non-parallel opposite faces.

Referring now to FIG. 2, there is shown schematically the preferred embodiment of the improved angular deviation measurement system of the present invention, being generally designated 10. The system 10 includes a source of incoherent light 12, such as incandescent lamp, which radiates light which is collected by a condensing lens 14 to illuminate a target slide 16. A projection lens 18 of the system 10 located one focal length from the target slide 16 on the side thereof opposite from the condensing lens 14, collimates the image of the target slide 16 and projects it through a test region, generally designated 20. A transparency 22 undergoing test, such as an aircraft windscreen, is shown inserted into the region 20.

The portion of the improved system 10 just described is positioned to the left of the transparency 22 such that the projection lens 18 is approximately at the observer (or design eye) position for the transparency 22 under test. The remainder of the improved system, the receiver portion, is located on the other (right) side of the transparency 22.

In order to compensate for lateral displacement of the image and thus eliminate an error source due to its passage at an oblique angle through the transparency 22, a collection or receiving lens 24 is positioned to the right of the transparency 22 for receiving the image projected through the transparency 22 from the projection lens 18. The light forming the image of the target slide 16 and focused by the receiving lens 24 one focal length to its right, is intercepted by a beam splitter 26 which divides the light into two channels of approximately equal intensities: one channel 28 to measure azimuth (horizontal) deviation, and the other channel 30 to measure elevation (vertical) deviation. Except for a 90° rotation about the optical axis 32 of the improved system 10, both channels are identical.

In each of the channels at the focal planes 34, 36 of the target slide image is positioned a linear detector device 38 and 40. Each device may take the form of a charge coupled device (CCD) linear (or one dimensional) array. A segment of the target slide image, to be described in greater detail hereinafter, intersects one of the CCD arrays 38, 40. The location of the intersection is detected by the respective CCD array and its associated electronics (not shown). The positional change or lateral shift of this intersection between when the transparency 22 is present in the test region 20 and when it is not is mathematically related to the angular deviation of the transparency 22 at the particular point being measured.

Turning now to FIG. 3, the target slide 16 is substantially opaque with a transparent pattern formed therein by a pair of transversely-aligned linear segments 44 and 46. In the illustrated embodiment of the slide 16, the transparent pattern is in the form of the letter "L" in which the linear segments 44, 46 are defined by the two legs of the "L" and are orthogonally aligned with one another. The dimensions and location of the "L"-shaped pattern are not particularly critical; however, the width of the legs of the"L" must be uniform to reduce error.

The image of the "L"-shaped pattern is produced at the respective focal planes 34, 36 in the channels 28, 30 by the combined effect of the receiving lens 24 and the beam splitter 26. Focal planes 34, 36 coincide with the linear light-receiving faces 48, 50 of the respective CCD arrays 38, 40. Therefore, the image of the "L"-shaped pattern is produced at the CCD faces.

Each of the linear segments or legs 44, 46 of the "L"-shaped pattern is offset from an optical axis 52, 54 in its respective channel 28, 30 so that only one of the linear segments or legs 44, 46 will intersect the one array in that particular channel, such as seen in FIGS. 4 and 5.

Figure 6:
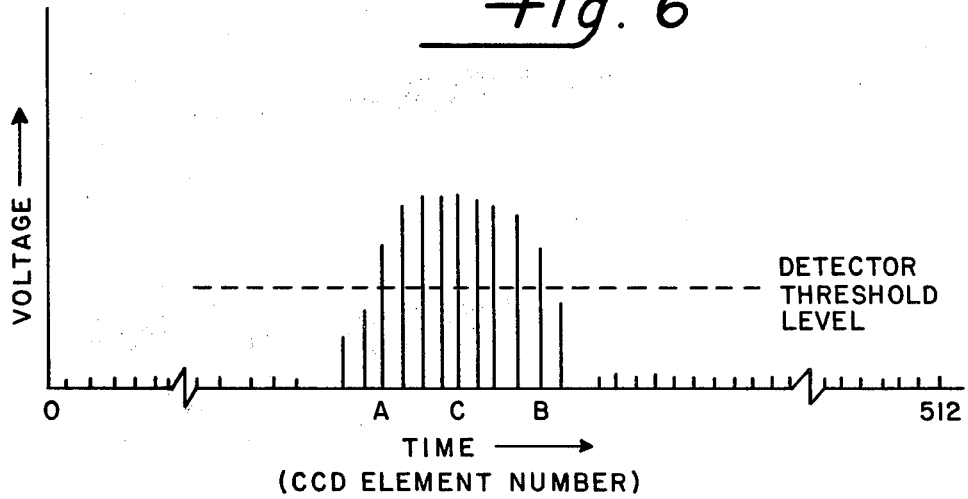
FIG. 6 is a schematical representation of the signal output from one of the detector arrays showing the pulses resulting from the intersection of the detector array and the image of the "L"-shaped transparent pattern of FIG. 4.

As the individual CCD arrays 38, 40 are sampled by use of an electrical circuit, such as the one disclosed by Kenneth L. Smith in patent application Ser. No. 118,007 U.S. Pat. No. 4,309,106 filed Feb. 4, 1981 and assigned to the assignee of the subject invention, the disclosure of which is incorporated by reference, the electronic output signal appears as shown in FIG. 6. Typically only a few CCD elements of the 512 elements of each array 38, 40 receive light forming the respective one of the segments or legs 44, 46 and are activated as shown by the series of spikes between A and B in FIG. 6.

To ascertain the location of the center position of the "L" segment or leg, a first counter in the circuit disclosed in the above-referenced '007 application counts CCD clock pulses until the signal output of the array exceeds a detection threshold voltage level. The first counter stops counting at this point (A) and a second counter starts counting. The second counter counts every other (or second) pulse until the output of the CCD array falls below the threshold voltage at point (B). The counts from both counters are added, and the total (or final) count corresponds to the CCD element number, from one end of the array, which corresponds to the location of the center of the "L" segment or leg. This position is shown at point (c) in FIG. 6. Equation (1) below shows this relationship:

$$C = A + [(B-A)/2] \quad (1)$$

where:
C = CCD element number of center position of "L" segment.
A = CCD element number of front edge of "L" segment.
B = CCD element number of back edge of "L" segment.

The accuracy capability of the improved system 10 is determined by the lens quality of the projection lens 18 and the receiving lens 24, the spacing of the CCD elements in each array and the focal length of the receiver lens 24. The minimum detectable angular deviation is determined by equation (2):

$$\alpha = \arctan(h/f_2) \quad (2)$$

where:
α = minimum measurable angle.
h = spacing between CCD array elements.
$f_2$ = focal length of receiver lens 24.

For one practical embodiment of the improved system, h was 0.025 mm and $f_2$ was 360 mm. Thus, from equation (2) the value of α was 0.07 mrad. It will be understood from equation (2) that the minimum measurable angular deviation can be improved by increasing the focal length, $f_2$, or decreasing the CCD element spacing. Also, in the embodiment mentioned, the diameter of the receiving lens was 25 mm, the distance between the lenses 18 and 24 was 1500 mm, and each CCD array was 12.5 mm long. The system used a 35 mm slide projector with a 75 mm focal length f/2.8 lens for the projector system. A 35 mm slide of a transparent "L"-shaped pattern was used as the target slide. The CCD element number readout was displayed on a three character segment display for each of the two channels.

It is thought that the invention and many of its attendant advantages will be understood from the foregoing description and it will be apparent that various changes may be made in the form, construction and arrangement of the parts thereof described without departing from the spirit and scope of the invention or sacrificing all of its material advantages, the form hereinbefore described being merely a preferred or exemplary embodiment thereof.

Having thus described the invention, what is claimed is:

1. In an improved system for measuring angular deviation in a transparency, the combination comprising:
   (a) an opaque object having a transparent pattern formed therein by a pair of transversely-aligned segments;
   (b) an incoherent light source for illuminating said object;
   (c) means for projecting an image of said transversely-aligned segments through a test region of space;
   (d) means for receiving said projected image and for transmitting it, after having removed any effects of lateral displacement of the image, into first and second channels; and
   (e) first and second linear detector arrays, each being positioned in one of said first and second channels for detecting a lateral shift in the position of the image of said transparent pattern segments due to angular deviation for a particular point on said transparency, the lateral shift occurring, if at all, when the transparency is inserted into the test area.

2. The angular deviation measuring system as recited in claim 1, wherein:
said first linear detector array is located in a focal plane of said image in said first channel such that one of said segments of said transparent pattern crosses said first array; and
said second linear detector array is located in a focal plane of said image in said second channel such that the other of said segments of said transparent pattern crosses said second array.

3. The angular deviation measuring system as recited in claims 1 or 2, wherein said transparent pattern is comprised by a pair of linear segments in the form of the letter "L" in which the segments are defined by the two legs of the "L" and are orthogonally aligned with one another.

4. In an improved system for measuring angular deviation in a transparency, such as the windscreen of an aircraft, the combination comprising:
   (a) a target in the form of an opaque slide with transparent "L"-shaped pattern;
   (b) an incoherent light source for illuminating said target;
   (c) means for forming and transmitting an image of said "L"-shaped pattern through said transparency and free of the effects of lateral displacement into a pair of orthogonally-arranged channels; and
   (d) a pair of linear CCD (charge coupled device) arrays, each array being located in one of said channels for detecting the position of the image of one leg of said "L"-shaped pattern after being transmitted through said transparency and into said channel and thereby facilitating measurement of azimuth and elevation components of angular deviation in said transparency.

5. The angular deviation measuring system as recited in claim 4, wherein said forming and transmitting means includes:

means for receiving light which passes through said target slide and for projecting an image of said transparent pattern of said slide through a test region of space containing said transparency; and means for receiving said image and for splitting the same into said channels after projection through said test region.

6. The angular deviation measuring system as recited in claims 4 or 5, wherein:

a first of said CCD arrays is positioned at a focal plane of said image in a first of said channels in crossing, orthogonal alignment with a first leg of said "L"-shaped pattern; and a second of said CCD arrays is positioned at a focal plane of said image in a second of said channels in crossing, orthogonal alignment with a second leg of said "L"-shaped pattern.

* * * * *